United States Patent
Kim et al.

(10) Patent No.: US 10,280,238 B2
(45) Date of Patent: May 7, 2019

(54) TRANSITION METAL COMPOUND, CATALYST COMPOSITION COMPRISING SAME, AND METHOD FOR PRODUCING OLEFIN POLYMER USING SAME

(71) Applicant: LG CHEM, LTD., Seoul (KR)

(72) Inventors: Byung Seok Kim, Daejeon (KR); Hee Kwang Park, Daejeon (KR); Kyung Seop Noh, Daejeon (KR); Sang Eun An, Daejeon (KR); In Sun Lee, Daejeon (KR); Hye Kyung Lee, Daejeon (KR); Sang Jin Jeon, Daejeon (KR); Ra Yun Choi, Daejeon (KR)

(73) Assignee: LG Chem, Ltd., Seoul (KR)

( * ) Notice: Subject to any disclaimer, the term of this patent is extended or adjusted under 35 U.S.C. 154(b) by 0 days.

(21) Appl. No.: 15/557,328

(22) PCT Filed: Jun. 28, 2016

(86) PCT No.: PCT/KR2016/006910
§ 371 (c)(1),
(2) Date: Sep. 11, 2017

(87) PCT Pub. No.: WO2017/034142
PCT Pub. Date: Mar. 2, 2017

(65) Prior Publication Data
US 2018/0105616 A1  Apr. 19, 2018

(30) Foreign Application Priority Data

Aug. 24, 2015  (KR) .................. 10-2015-0118902
Jan. 20, 2016  (KR) .................. 10-2016-0007128

(51) Int. Cl.
| | | |
|---|---|---|
| *C07F 17/00* | (2006.01) | |
| *C08F 4/6592* | (2006.01) | |
| *C08F 110/06* | (2006.01) | |
| *C08F 10/06* | (2006.01) | |
| *C07F 5/02* | (2006.01) | |
| *C07F 5/06* | (2006.01) | |
| *C07F 7/00* | (2006.01) | |
| *C07F 7/02* | (2006.01) | |
| *C07F 7/08* | (2006.01) | |
| *C08F 4/659* | (2006.01) | |

(52) U.S. Cl.
CPC ............ *C08F 10/06* (2013.01); *C07F 5/02* (2013.01); *C07F 5/06* (2013.01); *C07F 7/00* (2013.01); *C07F 7/02* (2013.01); *C07F 7/0803* (2013.01); *C07F 17/00* (2013.01); *C08F 4/65927* (2013.01); *C08F 110/06* (2013.01); *C08F 4/65912* (2013.01); *C08F 4/65916* (2013.01)

(58) Field of Classification Search
CPC .............. C08F 4/65927; C08F 4/65908; C08F 110/06; C07F 17/00
See application file for complete search history.

(56) References Cited

U.S. PATENT DOCUMENTS

| | | |
|---|---|---|
| 5,455,366 A | 10/1995 | Rohrmann et al. |
| 5,786,291 A | 7/1998 | Speca et al. |
| 5,831,105 A | 11/1998 | Aulbach et al. |
| 6,271,164 B1 | 8/2001 | Fritze et al. |
| 6,534,665 B1 | 3/2003 | Nunez et al. |
| 8,821,971 B2 | 9/2014 | Becker et al. |
| 2001/0053833 A1 | 12/2001 | Nakano et al. |
| 2006/0167295 A1 | 7/2006 | Damrau et al. |
| 2007/0043228 A1 | 2/2007 | Guidotti et al. |
| 2012/0123078 A1 | 5/2012 | Lee et al. |
| 2013/0131291 A1 | 5/2013 | Resconi et al. |
| 2014/0066288 A1 | 3/2014 | Lee et al. |
| 2014/0316085 A1 | 10/2014 | Stewart et al. |
| 2015/0031844 A1* | 1/2015 | Lee ............... C08F 4/65912 526/127 |
| 2015/0073107 A1 | 3/2015 | Choi et al. |
| 2016/0208028 A1 | 7/2016 | Choi et al. |

FOREIGN PATENT DOCUMENTS

| | | |
|---|---|---|
| EP | 1043339 A1 | 12/1998 |
| EP | 0953581 A1 | 4/1999 |
| EP | 2824107 A1 | 1/2015 |
| JP | 10204112 A | 8/1998 |
| JP | 2002128832 A | 5/2002 |
| JP | 3371118 B2 | 1/2003 |
| JP | 4234199 B2 | 3/2009 |
| JP | 4390770 B2 | 12/2009 |
| KR | 1020110013286 A | 2/2011 |
| KR | 1020120087706 A | 8/2012 |

(Continued)

OTHER PUBLICATIONS

Geoffrey W. Coates, Precise Control of Polyolefin Stereochemistry Using Single-Site Metal Catalysts, Chem. Rev., 2000, 100 (4), pp. 1223-1252.
Richard D. Adams, et al., Cyclobutyne Ligands. 5. C—H Bond Cleavage versus Ring Opening.., Organometallics 1994 13.
A. F. Asachenko, et al., 8-Methoxy-5-methyl-2,3-dihydro-1H-cyclopenta[a]naphthalene: synthesis and reactivity, Russian chemical bulletin, vol. 57, No. 12, pp. 2564.

*Primary Examiner* — Caixia Lu
(74) *Attorney, Agent, or Firm* — Dentons US LLP

(57) ABSTRACT

The present invention provides a transition metal compound, a catalyst composition comprising the same, and a method for producing an olefin polymer using the catalyst composition, the transition metal compound being capable of exhibiting high activity in olefin polymerization reaction, and also being capable of easily controlling the physical properties of an olefin polymer. When the transition metal compound is used, it is possible to provide an olefin polymer having an excellent energy-saving effect at the time of processing or molding.

13 Claims, No Drawings

(56) References Cited

FOREIGN PATENT DOCUMENTS

| KR | 1020130060208 A | 6/2013 |
|----|-----------------|--------|
| KR | 1020140133343 A | 11/2014 |
| KR | 1020150037652 A | 4/2015 |
| KR | 1020150058054 A | 5/2015 |
| WO | 99033882 A1 | 7/1999 |
| WO | 2004099225 A1 | 11/2004 |

* cited by examiner

TRANSITION METAL COMPOUND, CATALYST COMPOSITION COMPRISING SAME, AND METHOD FOR PRODUCING OLEFIN POLYMER USING SAME

CROSS-REFERENCE TO RELATED APPLICATION

This application is a National Stage Application of International Application No. PCT/KR2016/006910, filed Jun. 28, 2016, and claims the benefit of Korean Patent Application No. 10-2016-0007128 filed on Jan. 20, 2016 and Korean Patent Application No. 10-2015-0118902 filed on Aug. 24, 2015, contents of which are incorporated herein by reference in their entirety for all purposes as if fully set forth below.

TECHNICAL FIELD

The present invention relates to a transition metal compound, a catalyst composition comprising the transition metal compound, and a method for preparing olefin polymer using the catalyst composition.

BACKGROUND ART

In the existing commercial preparation process of polyolefin, Ziegler-Natta catalysts of titanium or vanadium compounds have been widely used, and although the Ziegler-Natta catalyst has high activity, it is a multi-active site catalyst and thus the molecular weight distribution of the produced polymer is wide and the compositional distribution of comonomers is not uniform, and thus, there is a limit to securing of desired properties.

Thus, recently, a metallocene catalyst in which a ligand comprising a cyclopentadiene functional group is bound to a transition metal such as titanium, zirconium, hafnium, etc. has been developed and widely used. The metallocene compound is generally activated with aluminoxane, borane, borate or other activators before use. For example, a metallocene compound having a ligand comprising a cyclopentadienyl group and two sigma chloride ligands uses aluminoxane as an activator. Such a metallocene catalyst is a single site catalyst having one kind of an active site, and is characterized by narrow molecular weight distribution of the produced polymer. Thus, since polyolefin polymerized with a metallocene catalyst has narrow molecular weight distribution, in case applied for some products, productivity was remarkably lowered due to extrusion load, etc., and thus, field application was difficult.

DISCLOSURE

Technical Problem

It is an object of the present invention to provide a transition metal compound that can provide olefin polymer with excellent energy reduction effect during processing or molding.

It is another object of the present invention to provide a catalyst composition comprising the transition metal compound and a method for preparing olefin polymer using the catalyst composition.

Technical Solution

According to one embodiment of the present invention, a transition metal compound represented by the following Chemical Formula 1 is provided:

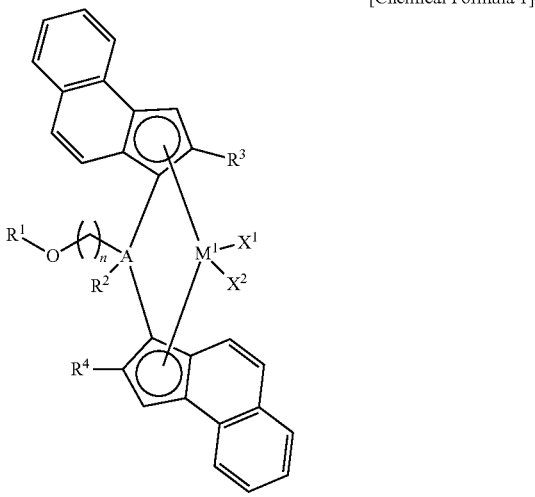

[Chemical Formula 1]

in the Chemical Formula 1, $M^1$ is a Group 3 transition metal, a Group 4 transition metal, a Group 5 transition metal, lanthanides transition metal or actinides transition metal, $X^1$ and $X^2$ are identical to or different from each other, and each independently, halogen or C1-20 alkyl, A is a Group 14 atom, n is an integer of 1 to 20, $R^1$ is C1-20 alkyl, C2-20 alkenyl, C7-30 alkylaryl, C7-30 arylalkyl, or C6-30 aryl, $R^2$ is hydrogen, C1-20 alkyl, C2-20 alkenyl, C7-30 alkylaryl, C7-30 arylalkyl, or C6-30 aryl, $R^3$ and $R^4$ are each independently, hydrogen, or C1-20 alkyl.

Specifically, in the Chemical Formula 1, $R^3$ and $R^4$ may be each independently, hydrogen, or C1-5 linear alkyl. In the Chemical Formula 1, $R^1$ may be C3-6 branched alkyl, and n may be an integer of 4 to 8. In the Chemical Formula 1, $R^2$ may be C1-6 linear alkyl.

In the Chemical Formula 1, $M^1$ may be Group 4 transition metal.

Meanwhile, according to another embodiment of the present invention, a catalyst composition comprising the transition metal compound represented by the Chemical Formula 1 is provided.

The catalyst composition may comprise one or more cocatalysts selected from the group consisting of the compounds represented by the following Chemical Formulas 2 to 4:

$R^6-[Al(R^5)-O]_m-R^7$  [Chemical Formula 2]

in the Chemical Formula 2, $R^5$, $R^6$ and $R^7$ are each independently, hydrogen, halogen, a C1-20 hydrocarbyl group, or a C1-20 hydrocarbyl group substituted with halogen, m is an integer of 2 or more, $D(R^8)_3$  [Chemical Formula 3]

in the Chemical Formula 3

D is aluminum or boron, $R^8$'s are each independently, halogen, a C1-20 hydrocarbyl group, a C1-20 hydrocarbyloxy group, or a C1-20 hydrocarbyl group substituted with halogen, $[L-H]^+[W(J)_4]^-$ or $[L]^+[W(J)_4]^-$  [Chemical Formula 4]

in the Chemical Formula 4,

L is neutral or cationic Lewis base,

W is a Group 13 atom, and J's are each independently, a C1-20 hydrocarbyl group; a C1-20 hydrocarbyloxy group;

or a C1-20 hydrocarbyl group or a C1-20 hydrocarbyloxy group of which one or more hydrogen atoms are substituted with one or more substituents selected from halogen, a C1-20 hydrocarbyloxy group and a C1-20 hydrocarbyl(oxy) silyl group.

Meanwhile, the catalyst composition may further comprise a carrier supporting the transition metal compound. As the carrier, silica, alumina, magnesia or a mixture thereof may be used.

For example, in case the catalyst composition further comprises a carrier supporting the transition metal compound, the catalyst composition may comprise the transition metal compound and the cocatalyst at a mole ratio of 10:1 to 1:1.

The catalyst composition may be used for propylene polymerization to provide polypropylene exhibiting low melting temperature and high melt flow rate, due to the unique conformation of the transition metal compound of the Chemical Formula 1.

Meanwhile, according to still another embodiment of the present invention, a method for preparing olefin polymer comprising the step of polymerizing olefin monomers in the presence of the above described catalyst composition, is provided.

Particularly, the method for preparing olefin polymer may use propylene as olefin monomers to provide propylene exhibiting low melting temperature and high melt flow rate. For example, the melting temperature of the polypropylene may be about 130° C. to 146° C., and the melt flow rate of polypropylene having a weight average molecular weight of 150,000 g/mol or less, measured at a temperature of 230° C. under a load of 2.16 kg, may be 70 g/10 min or more.

Effect of the Invention

According to the present invention, a transition metal compound that not only exhibits high activity for olefin polymerization, but also easily controls the properties of synthesized olefin polymer, a catalyst composition comprising the same, and a method for preparing olefin polymer using the catalyst composition are provided. Using the transition metal compound, olefin polymer with excellent energy reduction effect during processing or molding can be provided.

DETAILED DESCRIPTION OF THE EMBODIMENTS

Hereinafter, a transition metal compound, a catalyst composition comprising the same, and a method for preparing olefin polymer using the catalyst composition according to specific embodiments of the present invention will be explained.

According to one embodiment of the present invention, a transition metal compound represented by the following Chemical Formula 1 is provided:

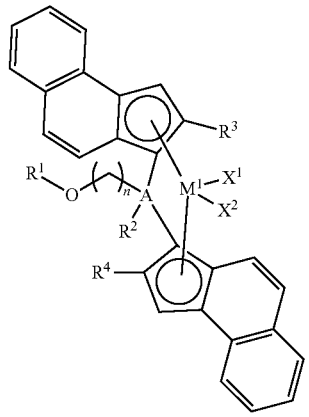

[Chemical Formula 1]

in the Chemical Formula 1, $M^1$ is a Group 3 transition metal, a Group 4 transition metal, a Group 5 transition metal, lanthanides transition metal or actinides transition metal, $X^1$ and $X^2$ are identical to or different from each other, and each independently, halogen or C1-20 alkyl, A is a Group 14 atom, n is an integer of 1 to 20, $R^1$ is C1-20 alkyl, C2-20 alkenyl, C7-30 alkylaryl, C7-30 arylalkyl, or C6-30 aryl, $R^2$ is hydrogen, C1-20 alkyl, C2-20 alkenyl, C7-30 alkylaryl, C7-30 arylalkyl, or C6-30 aryl, $R^3$ and $R^4$ are each independently, hydrogen, or C1-20 alkyl.

Unless specifically limited herein, the following terms may be defined as follows.

Halogen may be fluorine (F), chlorine (Cl), bromine (Br) or iodine (I).

A C1-20 alkyl may be linear, branched or cyclic alkyl. Specifically, the C1-20 alkyl may be C1-20 linear alkyl; C1-10 linear alkyl; C1-5 linear alkyl; C3-20 branched alkyl or cyclic alkyl; C3-15 branched or cyclic alkyl; or C3-10 branched or cyclic alkyl. More specifically, the C1-20 alkyl may be methyl, ethyl, n-propyl, iso-propyl, n-butyl, iso-butyl, tert-butyl, n-pentyl, iso-pentyl or cyclohexyl, etc.

A C2-20 alkenyl may be linear, branched or cyclic alkenyl. Specifically, the C2-20 alkenyl may be C2-20 linear alkenyl, C2-10 linear alkenyl, C2-5 linear alkenyl, C3-20 branched alkenyl, C3-15 branched alkenyl, C3-10 branched alkenyl, C5-20 cyclic alkenyl or C5-10 cyclic alkenyl. More specifically, the C2-20 alkenyl may be ethenyl, propenyl, butenyl, pentenyl, or cyclohexenyl, etc.

A C6-30 aryl means monocyclic, bicyclic or tricyclic aromatic hydrocarbon. Specifically, the C6-30 aryl may be phenyl, naphthyl or anthracenyl, etc.

A C7-30 alkylaryl means aryl of which one or more hydrogen atoms are substituted with alkyl. Specifically, the C7-30 alkylaryl may be methylphenyl, ethylphenyl, n-propylphenyl, iso-propylphenyl, n-butylphenyl, iso-butylphenyl, tert-butylphenyl, or cyclohexylphenyl, etc.

A C7-30 arylalkyl means alkyl of which one or more hydrogen atoms are substituted with aryl. Specifically, the C7-30 arylalkyl may be benzyl, phenylpropyl or phenylhexyl, etc.

The transition metal compound represented by the Chemical Formula 1 comprises two benzoindenyl groups as ligands, and has a structure wherein a functional group capable of acting as Lewis base is included in the bridge group connecting the two ligands as an oxygen donor. For example, if the transition metal compound with such a specific structure is activated by an appropriate method and used as a polymerization catalyst of olefin monomers, low melting temperature and high melt flow rate may be exhibited, and thus, olefin polymer with excellent energy reduction effect during processing or molding may be prepared. Particularly, as explained below, such an effect may be maximized when polymerizing propylene.

Specifically, in the transition metal compound represented by the Chemical Formula 1, the benzoindenyl ligand may be unsubstituted or may be substituted with a substituent having less steric hindrance. Thus, olefin polymer with the aimed conformation may be easily prepared while exhibiting good catalytic activity. For example, each of $R^3$ and $R^4$ in the Chemical Formula 1 may be independently hydrogen or C1-5 linear alkyl.

And, in the Chemical Formula 1, the bridge group connecting the benzoindenyl ligands may have an influence on the supporting stability of the transition metal compound. For example, for more improved supporting efficiency, $R^1$ in the Chemical Formula 1 may be C3-6 branched alkyl, and n may be an integer of 4 to 8. And, $R^2$ in the Chemical Formula 1 may be C1-6 linear alkyl.

Particularly, as the result of experiments of the present inventors, it was confirmed that olefin polymer capable of exhibiting excellent energy reduction effect during molding or processing can be prepared only through a transition metal compound in which ligands with the above explained structure are connected with a bridge group with the above explained structure as in the Chemical Formula 1, and that it cannot be prepared through a transition metal compound, even if it comprises ligands with the above explained structure, in which the ligands are not connected with a bridge group with the above explained structure.

Meanwhile, as $M^1$ in the Chemical Formula 1, Group 4 transition metal; or one of Ti, Zr and Hf may be used to improve storage stability of metal complex. And, $X^1$ and $X^2$ may be identical to or different from each other, and each independently, halogen or C1-20 alkyl; or each independently, halogen or C1-10 alkyl; or each independently, halogen.

The transition metal compound represented by the Chemical Formula 1 may be synthesized applying known reactions, and for more detailed synthesis method, Preparation Example 1 as described below may be referred to.

Meanwhile, according to another embodiment of the present invention, a catalyst composition comprising the transition metal compound represented by the Chemical Formula 1 is provided.

The catalyst composition may further comprise a cocatalyst capable of activating a transition metal compound. As such a cocatalyst, those commonly used in the technical field to which the present invention pertains may be used without specific limitations. For example, the cocatalyst may be one or more compounds selected from the group consisting of the compounds represented by the Chemical Formulas 2 to 4.

$$R^6-[Al(R^5)-O]_m-R^7 \quad \text{[Chemical Formula 2]}$$

in the Chemical Formula 2,
$R^5$, $R^6$ and $R^7$ may be each independently, hydrogen, halogen, a C1-20 hydrocarbyl group, or a C1-20 hydrocarbyl group substituted with halogen,
m is an integer of 2 or more, $$D(R^8)_3 \quad \text{[Chemical Formula 3]}$$

in the Chemical Formula 3,
D is aluminum or boron,
$R^8$'s are each independently, halogen, a C1-20 hydrocarbyl group, a C1-20 hydrocarbyloxy group, or a C1-20 hydrocarbyl group substituted with halogen, $$[L-H]^+[W(J)_4]^- \text{ or } [L]^+[W(J)_4]^- \quad \text{[Chemical Formula 4]}$$

in the Chemical Formula 4,
L is neutral or cationic Lewis base,
W is a Group 13 atom, and J's are each independently, a C1-20 hydrocarbyl group; a C1-20 hydrocarbyloxy group; or a C1-20 hydrocarbyl group or a C1-20 hydrocarbyloxy group of which one or more hydrogen atoms are substituted with one or more substituents selected from halogen, a C1-20 hydrocarbyloxy group and a C1-20 hydrocarbyl(oxy)silyl group.

Unless specifically limited herein, the following terms may be defined as follows.

A hydrocarbyl group is a monovalent functional group in which hydrogen atom is removed from hydrocarbon, and it may include an alkyl, an alkenyl, an alkynyl, an aryl, an aralkyl, an aralkenyl, an aralkynyl, an alkylaryl, an alkenylaryl, and an alkynylaryl groups, etc. And, a C1-20 hydrocarbyl group may be a C1-15 or C1-10 hydrocarbyl group. Specifically, a C1-20 hydrocarbyl group may be a linear, branched or cyclic alkyl group such as a methyl, an ethyl, an n-propyl, an iso-propyl, an an-butyl, an iso-butyl, a tert-butyl, an n-pentyl, an n-hexyl, an n-heptyl, a cyclohexyl groups, etc.; or an aryl group such as a phenyl, a naphthyl, an anthracenyl groups, etc.

A hydrocarbyloxy group is a functional group in which a hydrocarbyl group is bonded to oxygen. Specifically, a C1-20 hydrocarbyloxy group may be a C1-15 or C1-10 hydrocarbyloxyl group. More specifically, a C1-20 hydrocarbyloxy group may be a linear, branched or cyclic alkoxy group such as a methoxy, an ethoxy, an n-propoxy, an iso-propoxy, an n-butoxy, an iso-butoxy, a tert-butoxy, an n-pentoxy, an n-hexoxy, an n-heptoxy, a cyclohexoxy groups, etc.; or an aryloxy group such as a phenoxy, a naphthaleneoxy groups, etc.

A hydrocarbyl(oxy)silyl group is a functional group in which 1 to 3 hydrogen atoms of —$SiH_3$ are substituted with 1 to 3 hydrocarbyl groups or hydrocarbyloxy groups. Specifically, a C1-20 hydrocarbyl(oxy)silyl group may be a C1-15, C1-10, or C1-5 hydrocarbyl(oxy)silyl group. More specifically, a C1-20 hydrocarbyl(oxy)silyl group may be an alkylsilyl group such as a methylsilyl, a dimethylsilyl, a trimethylsilyl, a dimethylethylsilyl, a diethylmethylsilyl, a dimethylpropylsilyl groups, etc.; an alkoxysilyl group such as a methoxysilyl, a dimethoxysilyl, a trimethoxysilyl, a dimethoxyethoxysilyl groups, etc.; or an alkoxyalkylsilyl group such as a methoxydimethylsilyl, a diethoxymethylsilyl, a dimethoxypropylsilyl groups, etc.

Non-limiting examples of the compounds represented by the Chemical Formula 2 may include methylaluminoxane, ethylaluminoxane, isobutylaluminoxane, or tert-butylaluminoxane, etc. And, non-limiting examples of the compounds represented by the Chemical Formula 3 may include trimethylaluminum, triethylaluminum, tri isobutylaluminum, tripropylaluminum, tributylaluminum, dimethylchloroaluminum, triisopropylaluminum, tri-sec-butylaluminum, tricyclopentylaluminum, tripentylaluminum, triisopentylaluminum, trihexylaluminum, trioctylaluminum, ethyldimethylaluminum, methyldiethylaluminum, triphenylaluminum, tri-p-tolylaluminum, dimethylaluminum methoxide, dimethylaluminum ethoxide, etc. And, non-limiting examples of the compounds represented by the Chemical Formula 4 may include trimethylammonium tetrakis(pentafluorophenyl)borate, triethylammonium tetrakis(pentafluorophenyl)borate, N,N-dimethylanilinium tetrakis(pentafluorophenyl)borate, N,N-dimethylanilinium n-butyltris(pentafluorophenyl)borate, N,N-dimethylanilinium benzyltris(pentafluorophenyl)borate, N,N-dimethylanilinium tetrakis(4-(t-butyldimethylsilyl)-2,3,5,6-tetrafluorophenyl)borate, N,N-dimethylanilinium tetrakis(4-(triisopropylsilyl)-2,3,5,6-tetrafluorophenyl)borate, N,N-dimethylanilinium pentafluorophenoxytris(pentafluorophenyl)borate, N,N-dimethyl(2,4,6-trimethylanilinium)tetrakis(pentafluorophenyl)borate, trimethylammonium tetrakis(2,3,4,6-tetrafluorophenyl)borate, N,N-dimethylanilinium tetrakis(2,3,4,6-tetrafluorophenyl)borate, hexadecyldimethylammonium tetrakis(pentafluorophenyl)borate, N-methyl-N-dodecylanilinium tetrakis(pentafluorophenyl)borate or methyldi(dodecyl)ammonium tetrakis(pentafluorophenyl)borate, etc.

The catalyst composition may be a supported catalyst in which the above explained transition metal compound is supported on a carrier. Since the transition metal compound represented by the Chemical Formula 1 has the above explained structural characteristics, it can be stably supported on a carrier. And, the supported catalyst in which such a transition metal compound is supported exhibits high activity for olefin polymerization, and can easily provide low molecular weight olefin polymer.

As the carrier, carriers containing hydroxy groups or siloxane groups on the surface may be used. Specifically, as the carrier, carriers that is dried at high temperature to remove moisture on the surface, thus containing highly reactive hydroxy groups or siloxanes groups may be used. More specifically, as the carrier, silica, alumina, magnesia or a mixture thereof may be used. The carrier may be dried at high temperature, and commonly comprise oxide, carbonate, sulfate, nitrate components such as $Na_2O$, $K_2CO_3$, $BaSO_4$ and $Mg(NO_3)_2$, etc.

As explained above, when the catalyst composition is provided in the form of a supported catalyst, it can activate the transition metal compound according to the above embodiment even with a small amount. For example, in case the catalyst composition further comprises a carrier supporting the transition metal compound, the transition metal compound and the cocatalyst may be used at a mole ratio of 10:1 to 1:1.

The above explained catalyst composition may be used for the polymerization of olefin monomers to exhibit high catalytic activity, and can easily provide low molecular weight olefin polymer. Particularly, the catalyst composition may be used for the polymerization of propylene to exhibit much lower melting temperature and higher melt flow rate compared to the polymer of the same molecular weight, and thus, can provide polypropylene with excellent energy reduction efficiency during processing or molding.

Meanwhile, according to still another embodiment of the present invention, a method for preparing olefin polymer comprising the step of polymerizing olefin monomers in the presence of the catalyst composition is provided. As explained above, the catalyst composition, due to the specific structure, can easily provide low molecular weight olefin polymer compared to polyolefin polymerized using the existing metallocene catalyst, and exhibit higher activity when polymerizing olefin monomers.

Examples of the olefin monomers that can be polymerized with the catalyst composition may include ethylene, alpha-olefin, cyclic olefin, etc., and dien olefin monomers or trien olefin monomers, etc. having two or more double bonds can be also polymerized. Specific examples of the monomers may include ethylene, propylene, 1-butene, 1-pentene, 4-methyl-1-pentene, 1-hexene, 1-heptene, 1-octene, 1-decene, 1-undecene, 1-dodecene, 1-tetradecene, 1-hexadecene, 1-eicosene, norbornene, norbonadiene, ethylidene norbordene, phenyl norbordene, vinyl norbordene, dicylcopentadiene, 1,4-butadiene, 1,5-pentadiene, 1,6-hexadiene, styrene, alpha-methylstyrene, divinylbenzene, 3-chloromethlystyrene, etc., and two or more kinds of the monomers may be mixed and copolymerized.

The catalyst composition has excellent hydrogen reactivity even under the hydrogen feeding condition of the same amount, and thus, can provide olefin polymer having high flowability and narrow molecular weight distribution. For example, the olefin polymer prepared by the preparation method according to the above described another embodiment may have narrow molecular weight distribution of about 1.5 to 3, or about 1.5 to 2.5. Such olefin polymer has excellent impact resistance, strength, elasticity, etc., and exhibits excellent formability, and thus, it is expected to be applied for various products.

Particularly, the catalyst composition may be used for the polymerization of propylene to provide polypropylene having low melting temperature, due to the above explained specific structure of the transition metal compound of the Chemical Formula 1. Such propylene can be processed or molded at a relatively low temperature due to the low melting temperature, and thus, can provide various plastic products with less energy As the result of the experiments of the present inventors, it was confirmed that the melting temperature of polypropylene prepared using the above described catalyst composition is shown to be about 20° C. lower than polypropylene prepared using the previously known Ziegler-Natta catalyst, and is shown to be about 6° C. lower even than polypropylene prepared using the previously known metallocene catalyst. More specifically, polypropylene prepared using the above described catalyst composition may have a melting temperature of about 130° C. to 146° C. Thus, the catalyst composition may be usefully used particularly for the preparation of propylene polymer.

And, the catalyst composition may be used for propylene polymerization to provide polypropylene exhibiting high melt flow rate, due to the specific structure of the transition metal compound of the Chemical Formula 1. Such polypropylene has excellent flowability and processibility due to high melt flow rate, and thus, can remarkably increase the productivity of various plastic products.

More specifically, using the catalyst composition, polypropylene wherein the melt flow rate of polypropylene having weight average molecular weight of 150,000 g/mol or more, measured under at 230° C. under a load of 2.16 kg is 70 g/10 min or more, 80 g/10 min or more, 90 g/10 min or more, or 100 g/10 min or more, can be provided. The upper limit of the melt flow rate is not specifically limited, and for example, it may be controlled to about 150 g/10 min or less.

Meanwhile, for the polymerization of olefin monomers, various polymerization processes known as a polymerization reaction of olefin monomers, such as a continuous type solution polymerization process, a bulk polymerization process, a suspension polymerization process, a slurry polymerization process, or an emulsion polymerization process, etc. may be used.

Specifically, the polymerization reaction may be conducted at a temperature of about 50 to 110° C. or about 60 to 100° C. and a pressure of about 1 to 100 kgf/cm².

And, in the polymerization reaction, the catalyst composition may be used while being dissolved or diluted in a solvent such as pentane, hexane, heptanes, nonane, decane, toluene, benzene, dichloromethane, chlorobenzene, etc. Here, the solvent may be treated with a small amount of alkylaluminium, etc., thus removing a small amount of water or air, etc. that may have a bad influence on the catalyst in advance.

Since the olefin polymer prepared by the above described method is prepared using the above explained catalyst composition, it has low melting temperature, and thus, may exhibit excellent energy reduction effect during molding or processing.

Hereinafter, the actions and effects of the present invention will be explained in more detail with reference to the specific examples. However, these are presented only as the illustration of the invention and the scope of the present invention is not limited thereto.

Preparation Example 1: Preparation of a Transition Metal Compound and a Supported Catalyst Step 1: Preparation of 2-methyl-1H-benzoindene

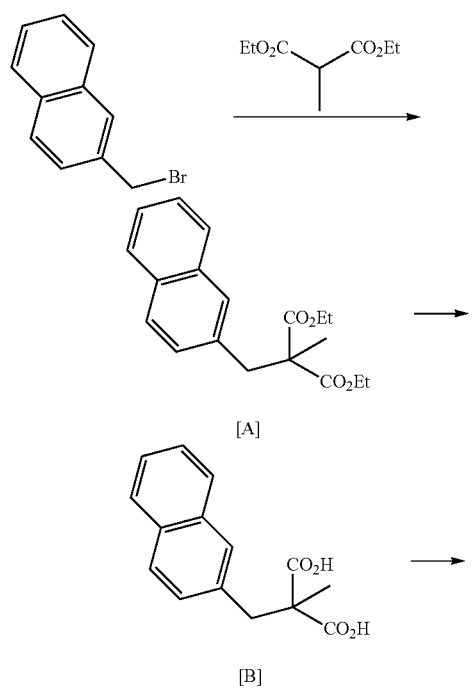

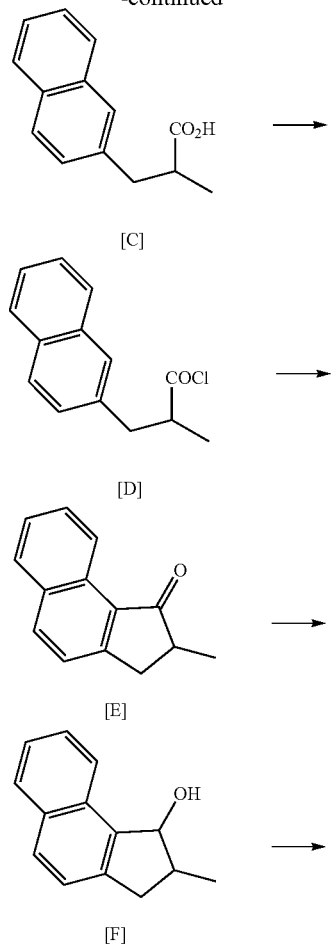

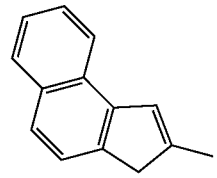

1.1 g of NaH and 9.1 mL of diethyl methylmalonate were added to 55 mL of THF (tetrahydrofuran), and then, the reaction mixture was refluxed for 1 hour. Thereafter, the reaction mixture was cooled to room temperature, 10g of 2-bromomethylnaphthalene was added thereto, and the reaction mixture was refluxed again for 3 hours to prepare a compound A.

Subsequently, to 13.6 g of the reaction mixture comprising the compound A, 30 mL of ethanol and 9.7 g of KOH dissolved in 29 mL of water were added, and the reaction mixture was refluxed for 4 hours to obtain a compound B.

Thereafter, to the reaction mixture comprising the compound B, HCl was added, and then, an organic layer was extracted with ethyl acetate. Thereafter, the organic layer was dried, and then, heated until gas did not come out (heated to about 175° C.) to obtain a compound C.

And, the compound C was dissolved in 24.5 mL of dichloromethane, 7.2 mL of thionyl chloride was added thereto, and then, the reaction mixture was refluxed for 30 minutes to obtain a compound D.

Thereafter, the reaction mixture comprising the compound D was dried to remove the solvent. And, the remaining solutes were added to 10 mL of dichloromethane, and then, the reaction mixture was cooled to 0° C. Into the cooled reaction mixture, 5.2 g of aluminum chloride dispersed in 40 mL of dichloromethane was slowly introduced over 30 minutes. Subsequently, the obtained reaction mixture was refluxed for 30 minutes, and an organic layer was extracted with a HCl aqueous solution and dichloromethane, thus obtaining a compound E.

Thereafter, 2.1 g of the compound E was dissolved in 12 mL of THF and 6 mL of methanol to prepare a reaction mixture. And, at a temperature of 0° C., into a reactor containing 809 mg of NaBH$_4$ powder, the reaction mixture was slowly introduced for 1 hour. Subsequently, the reaction mixture was stirred at room temperature for 1 hour, and an organic layer was extracted with water, thus obtaining a compound F.

Thereafter, 2.1 g of the compound F was dissolved in 13 mL of toluene, 102 mg of para-toluenesulfonic acid was introduced therein, and the reaction mixture was refluxed. The progress of the reaction was confirmed with TLC (thin layer chromatography), and if the reaction was finished, an organic layer was extracted with an aqueous solution of NaCO$_3$ and diethylether, thus obtaining 2-ethyl-1H-benzoindene.

Step 2: Preparation of (6-t-buxotyhexyl)dichloromethylsilane

Into a 1 L flask, 95 g of Mg was put and washed three times with 1.0M HCl, three times with MeOH and three times with acetone, and then, dried under reduced pressure at 25° C. for 3 hours. Into the reactor containing the dried Mg, 1.0 L of THF, and 5.0 mL of 1,2-DBE (1,2-dibromoethane) were sequentially introduced, and the mixture was stirred. Into a dropping funnel, 500 g of t-buxotyhexyl chloride was introduced, and then, about 5% thereof was introduced into the reactor for 5 minutes. Thereafter, the temperature of the reactor was raised to 70° C., and the reaction mixture was stirred for 30 minutes. Subsequently, the remaining amount of t-buxotyhexyl chloride was slowly introduced into the reactor over about 3 hours, and the reaction mixture was stirred at 70° C. for about 15 hours. Thereafter, the reactor was cooled to 25° C., the reaction mixture was filtered to remove an excessive amount of Mg, and the filtrate was transferred to a 3 L flask.

Meanwhile, the reactor was washed and dried under reduced pressure, and then, 583 g of trichloromethylsilane and 3.3 L of THF were introduced into the reactor, and the reactor was cooled to −15° C. Thereafter, to the reactor, the above prepared filtrate was slowly added dropwise while maintaining at −5° C. for 2 hours. The temperature of the reactor was raised to 25° C., and the reaction mixture was stirred at about 130 rpm for 16 hours. Thereafter, the reaction mixture was vacuum distilled at 25° C., and dispersed in 4.3 L of hexane, and then, stirred for 30 minutes. Thereafter, solid was filtered from the reaction mixture, and then, the reaction mixture was additionally washed with 1.0 L of hexane and filtered, and the filtrate was vacuum distilled at 25° C. to obtain (6-t-buxotyhexyl) dichloromethylsilane with the yield of 85%.

$^1$H NMR (500 MHz, CDCl$_3$, 7.24 ppm): 0.76 (3H, s), 1.11 (2H, t), 1.18 (9H, s), 1.32~1.55 (8H, m), 3.33 (2H, t)

Step 3: Preparation of bis(2-methyl-1H-benzoinden-1-yl)(6-(t-butoxy(hexyl)(methyl)silane 2 g (11.1 mmol) of 2-methyl-1H-benzoindene was dissolved in a solvent mixture of 101 mL of toluene and 10.1 mL of THF. Thereafter, the reaction mixture was cooled to −25° C., and 4.7 mL of an n-butyl lithium solution (2.5M solution in hexane) was slowly added dropwise to the reaction mixture. Subsequently, the obtained reaction mixture was stirred at room temperature for 3 hours. And, 9.9 mg of CuCN was dissolved in a small amount of toluene and added to the reaction mixture in the form of slurry, and the reaction mixture was stirred for 30 minutes. Subsequently, 1.6 g of the above prepared (6-t-butoxyhexyl)dichloromethylsilane was added to the reaction mixture, and the obtained reaction mixture was stirred at room temperature for a day. Thereafter, an organic layer was extracted from the obtained reaction mixture with water and methyl t-butyl ether, and dried to obtain a ligand.

Step 4: Preparation of bis(2-methyl-1H-benzoinden-1-yl)(6-(t-butoxy)hexyl)(methyl)silane zirconium dichloride 3.1 g (5.55 mmol) of the above prepared bis(2-methyl-1H-benzoinden-1-yl)(6-(t-butoxy)hexyl)(methyl)silane was dissolved in 55.5 mL of diethyl ether, and then, 4.7 mL of an n-butyl lithium solution (2.5M solution in hexane) was slowly added dropwise at −25° C. Thereafter, the obtained reaction mixture was stirred at room temperature for about 3 hours, and then, cooled again to −25° C. And, to a reactor containing 2.09 g of bis(tetrahydrofurane) zirconium tetrachloride [ZrCl$_4$(C$_4$H$_5$O)$_2$], the reaction mixture was added, and stirred at room temperature for a day. Thereafter, the reaction mixture was dried to remove the solvent, and then, dichloromethane was introduced. And, the obtained solution mixture was filtered and the filtrate was dried. And, the solid obtained by drying was recrystallized at −30° C. with toluene to obtain a transition metal compound with the yield of 17%.

$^1$H NMR (500 MHz, CDCl$_3$, 7.26 ppm): 1.19 (9H, s), 1.49~1.52 (2H, m), 1.59~1.62 (2H, m), 1.66~1.67 (2H, m), 1.84~1.86 (4H, m), 2.35 (6H, s), 3.37 (2H, t), 7.26 (2H, s), 7.36 (2H, dd), 7.48 (2H, t), 7.51 (2H, t), 7.55 (2H, dd), 7.76 (2H, d), 7.94 (2H, d).

Step 5: Preparation of a Supported Catalyst

Into a shrink flask containing 3 g of silica, 30 mmol of methylaluminoxane (MAO) was put and reacted at 90° C. for 24 hours. After the reaction was finished, if the reaction product settled, the solution of the upper layer was removed and the remaining precipitate was washed with toluene one time. And, 180 umol of the transition metal compound prepared above was dissolved in toluene and introduced into the flask, and reacted at 70° C. for 5 hours. After the reaction was finished, if the reaction product settled, the solution of the upper layer was removed, and the remaining precipitate was washed with toluene one time. Thereafter, into the flask, 144 umol of dimethylanilinium tetrakis(pentafluorophenyl) borate was put, and reacted at 70° C. for 5 hours. After the reaction was finished, the reaction mixture was washed with toluene and washed again with hexane, and then, vacuum dried to obtain a silica supported metallocene catalyst in the form of solid particles.

Preparation Example 2: Preparation of a Transition Metal Compound and a Supported Catalyst 3.1 g (5.55 mmol) of bis(2-methyl-1H-benzoinden-1-yl)(6-(t-buxoty)hexyl)(methyl)silane prepared in the Step 3 of the Preparation Example 1 was dissolved in 55.5 mL of diethyl ether, and then, 4.7 mL of an n-butyl lithium solution (2.5M solution in hexane) was slowly added dropwise at −25° C. Thereafter, the obtained reaction mixture was stirred at room temperature for about 3 hours, and then, cooled again to −25° C. And, to a reactor containing 1.78 g of hafnium tetrachloride (HfCl$_4$), the reaction mixture was added and stirred at room temperature for a day. Thereafter, the reaction mixture was dried to remove a solvent, and then, dichloromethane was introduced. And, the obtained solution mixture was filtered and the filtrate was dried. And, the solid obtained by drying was recrystallized with toluene at −30° C. to obtain a transition metal compound with the yield of 12%.

$^1$H NMR (500 MHz, CDCl$_3$, 7.26 ppm): 1.20 (9H, s), 1.50~1.54 (2H, m), 1.59~1.63 (2H, m), 1.67~1.69 (2H, m), 1.81~1.87 (4H, m), 2.45 (6H, d), 3.38 (2H, t), 7.19 (2H, s), 7.33 (2H, dd), 7.48 (2H, t), 7.53 (2H, t), 7.60 (2H, dd), 7.77 (2H, d), 7.92 (2H, d).

Using the above prepared transition metal compound, a supported catalyst was prepared by the same method as the Step 5 of the Preparation Example 1.

Example 1: Polymerization of Olefin Monomers

First, a 2 L stainless reactor was vacuum dried at 65° C. and then cooled, 3 mL of triethylaluminum was introduced therein at room temperature, and 770 g of propylene was introduced therein. It was stirred for 10 minutes, and then, 45 mg of the supported catalyst prepared in Preparation Example 1 was dispersed in 20 mL of hexane and prepared in the form of slurry, which was introduced in the reactor using nitrogen pressure. Here, about 331 ppm of hydrogen gas was introduced together with the catalyst. Thereafter, the temperature of the reactor was slowly raised to 70° C., and then, polymerization was conducted for 1 hour. After the reaction was finished, unreacted propylene was vented.

Example 2: Polymerization of Olefin Monomers

First, a 2 L stainless reactor was vacuum dried at 65° C. and then cooled, 3 mL of triethylaluminum was introduced therein at room temperature, and 770 g of propylene was introduced therein. It was stirred for 10 minutes, and then, 45 mg of the supported catalyst prepared in Preparation Example 2 was dispersed in 20 mL of hexane and prepared in the form of slurry, which was introduced in the reactor using nitrogen pressure. Here, about 331 ppm of hydrogen gas was introduced together with the catalyst. Thereafter, the temperature of the reactor was slowly raised to 70° C., and then, polymerization was conducted for 1 hour. After the reaction was finished, unreacted propylene was vented.

Example 3: Polymerization of Olefin Monomers

First, a 2 L stainless reactor was vacuum dried at 65° C. and then cooled, 3 mL of triethylaluminum was introduced therein at room temperature, and 770 g of propylene and 12,000 cc of ethylene were introduced therein. It was stirred for 10 minutes, and then, 30 mg of the supported catalyst prepared in Preparation Example 1 was dispersed in 20 mL of hexane and prepared in the form of slurry, which was introduced in the reactor using nitrogen pressure. Here, about 331 ppm of hydrogen gas was introduced together with the catalyst. Thereafter, the temperature of the reactor was slowly raised to 70° C., and then, polymerization was conducted for 1 hour. After the reaction was finished, unreacted propylene was vented.

Example 4: Polymerization of Olefin Monomers

First, a 2 L stainless reactor was vacuum dried at 65° C. and then cooled, 3 mL of triethylaluminum was introduced therein at room temperature, and 770 g of propylene and 12,000 cc of ethylene were introduced therein. The reaction mixture was stirred for 10 minutes, and then, 30 mg of the supported catalyst prepared in Preparation Example 2 was dispersed in 20 mL of hexane and prepared in the form of slurry, which was introduced in the reactor using nitrogen pressure. Here, about 331 ppm of hydrogen gas was introduced together with the catalyst. Thereafter, the temperature of the reactor was slowly raised to 70° C., and then, polymerization was conducted for 1 hour. After the reaction was finished, unreacted propylene was vented.

Comparative Example 1: Polymerization of Olefin Monomers

Using a transition metal compound represented by the following Chemical Formula P1, a supported catalyst was prepared by the same method as the Step 5 of Preparation Example 1.

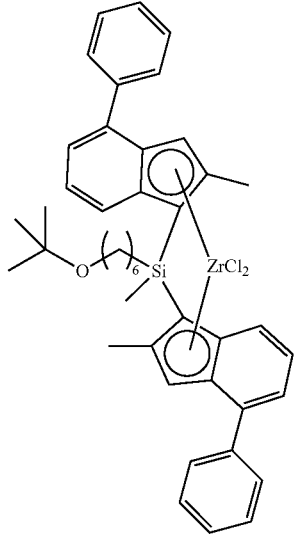

[Chemical Formula P1]

And, using a supported catalyst comprising the transition metal compound of the Chemical Formula P1, olefin monomers were polymerized. Since the optimum conditions for the polymerization of olefin monomers vary according to the kind of catalysts, olefin monomers were polymerized under conditions optimized for the supported catalyst comprising the transition metal compound of the Chemical Formula P1.

Specifically, a 2 L stainless reactor was vacuum dried at 65° C. and then cooled, 3 mL of triethylaluminum was introduced therein at room temperature, and 1.5 L of propylene was introduced therein. It was stirred for 10 minutes, and then, the supported catalyst comprising the transition metal compound of the Chemical Formula P1 was introduced in the reactor with nitrogen pressure. Here, about 370 ppm of hydrogen gas was introduced together with the catalyst. Thereafter, the temperature of the reactor was slowly raised to 70° C., and then, polymerization was conducted for 1 hour. After the reaction was finished, unreacted propylene was vented.

Comparative Example 2: Polymerization of Olefin Monomers

Using a transition metal compound represented by the following Chemical Formula P2, olefin monomers were polymerized. Since the transition metal compound of the Chemical Formula P2 has low supporting stability, it was activated by an excessive amount of cocatalyst before use, as follow.

[Chemical Formula P2]

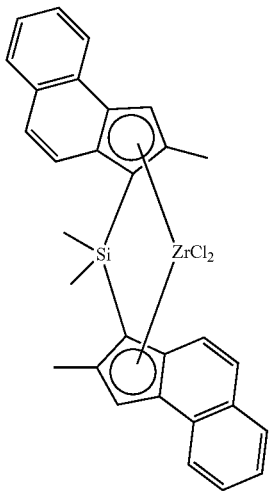

Specifically, a 16 L reactor was washed with nitrogen, and filled with 10 L of liquid propylene. 40 mmol of methylaluminoxane (MAO) was dissolved in toluene and introduced into the reactor, and the solution was stirred at 30° C. for 15 minutes. Meanwhile, 20 mmol of methylaluminoxane (MAO) and 5.2 mg (9 umol) of the transition metal compound of the Chemical Formula P2 were introduced into toluene, and the solution was allowed to stand for 15 minutes. And, the solution was introduced into the reactor. Thereafter, the temperature of the reactor was slowly raised to 70° C., and then, propylene was polymerized for 1 hour.

Experimental Example: Evaluation of the Properties of Olefin Polymer

The properties of the olefin polymer prepared in Examples 1 to 4 and Comparative Examples 1 to 2 were measured as follows, and shown in the following Table 1.

(1) Measurement of MFR (melt flow rate): MFR was measured according to ISO 1133 at a temperature of 230° C. and under a load of 2.16 kg using olefin polymer of which MFR is to be measured.

(2) Measurement of Tm (melting temperature): Using a differential scanning calorimeter (DSC, manufactured by TA instruments), olefin polymer of which Tm is to be measured was filled in an aluminum pan, and the temperature of the second endothermic curve peak obtained when the temperature was raised to 200° C. at 10° C./min and maintained at 200° C. for 5 minutes, and then, decreased to 30° C. at −10° C./min, and subsequently, raised to 200° C. at 10° C./min, was determined as a melting temperature (Tm).

TABLE 1

|  | Example 1 | Example 2 | Example 3 | Example 4 | Comparative Example 1 | Comparative Example 2 |
| --- | --- | --- | --- | --- | --- | --- |
| Weight average molecular weight [g/mol] | 95,000 | 106,000 | 101,000 | 403,000 | 145,000 | 330,000 |
| Melt flow rate [g/10 min] | 110 | 100 | 88 | 4 | 60 | 5.6 |
| Melting temperature [° C.] | 143 | 145 | 134 | 138 | 149 | 147 |

The invention claimed is:
1. A transition metal compound represented by the following Chemical Formula 1:

[Chemical Formula 1]

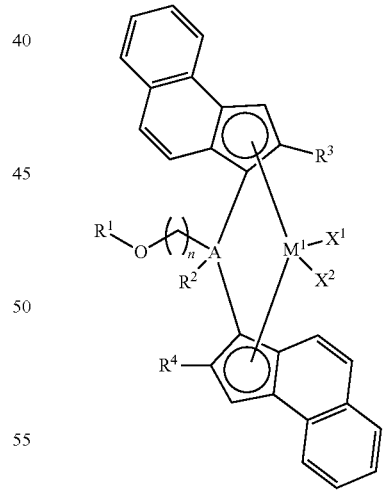

in the Chemical Formula 1,
M$^1$ is Group 3 transition metal, Group 4 transition metal, Group 5 transition metal, lanthanides transition metal or actinides transition metal,
X$^1$ and X$^2$ are identical to or different from each other, and each independently, halogen or C1-20 alkyl,
A is a Group 14 atom, n is an integer of 1 to 20,
R$^1$ is C1-20 alkyl, C2-20 alkenyl, C7-30 alkylaryl, C7-30 arylalkyl, or C6-30 aryl, $R^2$ is hydrogen, C1-20 alkyl, C2-20 alkenyl, C7-30 alkylaryl, C7-30 arylalkyl, or C6-30 aryl, $R^3$ and $R^4$ are each independently hydrogen, or C1-20 alkyl.

2. The transition metal compound according to claim 1, wherein $R^3$ and $R^4$ are each independently hydrogen, or C1-5 linear alkyl.

3. The transition metal compound according to claim 1, wherein $R^1$ is C3-6 branched alkyl, and n is 4 to 8.

4. The transition metal compound according to claim 1, wherein $R^2$ is C1-6 linear alkyl.

5. The transition metal compound according to claim 1, wherein $M^1$ is Group 4 transition metal.

6. A catalyst composition comprising the transition metal compound represented by the Chemical Formula 1 of claim 1.

7. The catalyst composition according to claim 6, wherein the catalyst composition comprises one or more cocatalysts selected from the group consisting of the compounds represented by the following Chemical Formulas 2, 3, and 4:

   [Chemical Formula 2]

in the Chemical Formula 2, $R^5$, $R^6$ and $R^7$ are each independently[M] hydrogen, halogen, a C1-20 hydrocarbyl group, or a C1-20 hydrocarbyl group substituted with halogen, m is an integer of 2 or more,

   [Chemical Formula 3]

in the Chemical Formula 3

D is aluminum or boron, $R^8$'s are each independently halogen, a C1-20 hydrocarbyl group, a C1-20 hydrocarbyloxy group, or a C1-20 hydrocarbyl group substituted with halogen,

   [Chemical Formula 4]

in the Chemical Formula 4,

L is neutral or cationic Lewis base,

W is a Group 13 atom, and J's are each independently a C1-20 hydrocarbyl group; a C1-20 hydrocarbyloxy group; or a C1-20 hydrocarbyl group or a C1-20 hydrocarbyloxy group of which one or more hydrogen atoms are substituted with one or more substituents selected from halogen, a C1-20 hydrocarbyloxy group and a C1-20 hydrocarbyl(oxy)silyl group.

8. The catalyst composition according to claim 6, further comprising s carrier supporting the transition metal compound.

9. The catalyst composition according to claim 8, wherein the carrier is silica, alumina, magnesia or a mixture thereof.

10. The catalyst composition according to claim 7, wherein the catalyst composition further comprises a carrier supporting the transition metal compound, and the mole ratio of the transition metal compound and the cocatalyst is 10:1 to 1:1.

11. A method for preparing olefin polymer comprising the step of polymerizing olefin monomers in the presence of the catalyst composition of claim 6.

12. The method according to claim 11, wherein the olefin monomer is propylene.

13. The method according to claim 12, wherein polypropylene having a melting temperature of 130° C. to 146° C. is provided.

* * * * *